(12) United States Patent
Griesmer et al.

(10) Patent No.: US 6,472,668 B1
(45) Date of Patent: Oct. 29, 2002

(54) HIGH VOLTAGE DISTRIBUTION SYSTEM FOR CZT ARRAYS

(75) Inventors: Jerome J. Griesmer, Kirtland; Barry Kline, Cleveland Hts., both of OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 18 days.

(21) Appl. No.: 09/722,124

(22) Filed: Nov. 24, 2000

(51) Int. Cl.$^7$ ................................................ G01T 1/20
(52) U.S. Cl. .......................... 250/370.13; 250/338.4; 250/332; 250/370.01
(58) Field of Search ..................... 250/370.13, 338.4, 250/332, 370.01

(56) References Cited

U.S. PATENT DOCUMENTS

| | | | |
|---|---|---|---|
| 4,090,080 A | | 5/1978 | Tosswill |
| 4,262,207 A | | 4/1981 | Tosswill |
| 4,443,701 A | * | 4/1984 | Bailey ..................... 250/338.4 |
| 4,982,096 A | | 1/1991 | Fujii |
| 5,077,770 A | | 12/1991 | Sammon |
| 5,967,983 A | | 10/1999 | Ashburn |
| 5,991,357 A | | 11/1999 | Marcovici |
| 6,046,454 A | | 4/2000 | Lingren et al. |
| 6,055,450 A | | 4/2000 | Ashburn |
| 6,091,070 A | | 7/2000 | Lingren et al. |

OTHER PUBLICATIONS

G.L. Zeng, et al. "Eigen Analysis of Cone–Beam Scanning Geometries." *Three–Dimensional Image Reconstruction in Radiation and Nuclear Medicine* © 1996 by Kluwer Academic Publishers, Netherlands. pp. 75–86.

G.L. Zeng, et al., "A cone beam tomography algorithm for orthogonal circle–and–line orbit." *Phys. Med. Biol.*, 1992, vol. 37, No. 3, 563–577.

S.Webb, et al., "Monte Carlo modeling of the performance of a rotating circle–slit–collimator for improved planar gamma–camara imaging," *Phys.Med. Biol.*, vol. 37, No. 5, 1095–1108, 1992.

(List continued on next page.)

*Primary Examiner*—Constantine Hannaher
*Assistant Examiner*—Andrew Israel
(74) *Attorney, Agent, or Firm*—Fay, Sharpe, Fagan, Minnich & McKee, LLP

(57) ABSTRACT

A subject (10) is disposed adjacent a detector array (18). The subject (10) is injected with a radioactive isotope (14) and γ-ray emissions indicative of nuclear decay are detected at the detector array (18). The detector array generates electrical signals in response to each γ-ray which signals are processed (64) and reconstructed (46) into an image representation of the anatomy of the subject (10). A high voltage bias is applied across the detector array. The bias is applied by a set of bias strips (80) and an electrically isolated common busbar (82) built onto a sheet of flexible circuit material. This flexible circuit (81) is highly transmissive to gamma radiation in the energy range 60–180 keV which is typically used in diagnostic nuclear medicine. Connections between the common busbar (82) and the bias strips (80) are made by resistors (92) on individual detector cards. Each bias strip is capacitively coupled (68) to the local ground on each detector card to form a Faraday shield around each detector array. Bias strips set above groups of detector arrays and electrical pads (86) are disposed along opposite faces. A substantially uniform DC electric field is set up between the strips and pads across the detector array. The strips and pads substantially surround groups of arrays defining Faraday cages. Capacitive filters (68) connected with the strips filter out noise. The capacitor's connection to the P-ASIC ground completes a Faraday shield around the highly sensitive detector array (18). Resistors (92) electrically isolate each of the Faraday cages. Additionally, light baffles are added to prevent visible light from generating a signal in the detector array (18). Collimator vanes (16) are supported on a ground layer (100) which is separated from the conductive strips (80) by a resilient foam layer (102).

22 Claims, 6 Drawing Sheets

OTHER PUBLICATIONS

Mauderli, et al., "A Computerized Rotating Laminar Radionuclide Camera." *J. Nucl. Med.* 20: :341–344 (1979).

Entine, et al., "Cadmium Telluride Gamma Camera," *IEEE Transactions on Phys.* vol. NS–26, No. 1:552–558 (1979).

Urie, et al., "Rotating Laminar Emission Camera with GE–detector," *Med. Phys.* 8(6) :865–870 (1981).

Mauderli, et al., "Rotating Laminar Emission Camera with GE–detector," *Med Phys.* 8(6) :861–876 (1981).

Malm, et al., "A Germanium Laminar Emission Camera," *IEEE Transactions on Nuclear Science*, vol. NS–29, No.1:465–468m (1982).

Mauderli, et al., "Rotating Laminar Emission Camera with GE–Detector: Further Developments," *Med. Phys.* 14(6):1027–1031 (1987).

* cited by examiner

HIGH VOLTAGE DISTRIBUTION SYSTEM FOR CZT ARRAYS

BACKGROUND OF THE INVENTION

The present invention deals with the nuclear camera arts. It finds particular application in conjunction with electronics used in SPECT cameras and will be described with particular reference thereto. However, it is to be appreciated that the present invention may find application in PET cameras and other radiation detection systems in which high voltage biases are applied to detector arrays.

Nuclear imaging employs a source of radioactivity to image the anatomy of a subject. Typically, a radiopharmaceutical is injected into the patient. This source contains atoms that decay at a predictable rate. Each time an atom decays, it releases a γ-ray. These γ-rays are detected, and from information such as its position and energy, a representation of the interior of the subject is reconstructed.

Typically, a nuclear camera has one, two, or three detector heads. Each head has a large scintillator sheet, such as doped sodium iodide, which converts incident radiation into scintillations, i.e. flashes of light. An array of photomultiplier tubes is disposed in back of the scintillator to monitor for light flashes. The output of the photomultiplier tubes and associated circuitry indicates the coordinates of each scintillation on the sodium iodide crystal and its energy. Unfortunately, there are numerous non-uniformities and inaccuracies when using a large scintillator crystal and an array of photomultiplier tubes.

Rather than using a single, large scintillator and photomultiplier tubes, others have proposed using an array of small scintillators, each associated with a photodiode or other photoelectrical device which senses a scintillation in each individual scintillation crystal. Other types of individual solid-state detectors have also been suggested.

Solid state radiation detectors utilize the photoelectric effect to detect radiation. That is, received radiation photons liberate electrons from their orbits around atoms of the target material. The electrons are detected as an electrical signal. Electrons released by a single photon typically generate a weak signal that is amplified. Typically, a high bias voltage is applied across the detector material to aid the photoelectric phenomenon. These voltages typically are several hundreds of volts. With such high biases, these systems become sensitive to electrical noise, and ambient photoelectric radiation, such as visible light. Because of this sensitivity, noise in the bias or stray light/radiation can be mistaken for events for which the detector is looking.

The present invention provides a new and improved method and apparatus that overcomes the above referenced problems and others.

SUMMARY OF THE INVENTION

In accordance with one aspect of the present invention, a nuclear imaging apparatus is given. A detector system detects γ-rays and generates electrical signals in response. A Faraday cage shields the detector system. Downstream electronics process the electrical signals that the detector system generates, and a reconstruction processor reconstructs the electrical signals into an image representation.

In accordance with another aspect of the present invention, a nuclear camera is given. A plurality of solid state arrays respond to incoming γ-irradiation by releasing electrons. Conductive strips provide a bias to the arrays. Conductive pads lie opposite the conductive strips. A voltage source supplies power to the conductive strips, setting up an electric field, attracting electrons to the conductive pads. Signal processing circuitry provides information about electronic activity to a reconstruction processor that processes the data into an image representation.

In accordance with another aspect of the present invention, a radiation detector assembly is given. An array of detectors that detects high energy radiation is biased by a bias circuit that applies a high voltage potential between opposite faces of the detector array. An electrically insulating layer and a ground layer are mounted on a radiation receiving side of the bias circuit. High-z metal vanes collimate incumbent radiation.

In accordance with another aspect of the present invention, a method of nuclear imaging is given. A bias voltage is applied to a solid state detector array, and is filtered to remove noise. Response is given to incident radiation by generating a current pulse. The current pulses are processed and reconstructed into an image representation.

One advantage of the present invention is that it allows for accurate detection of radiation events.

Another advantage of the present invention is that reduces noise in large bias voltages.

Yet another advantage of the present invention is that it reduces the chance of the system being affected by ambient photoelectric radiation.

Yet another advantage of the present invention is the ease of assembly of the detector system and disassembly for servicing the system.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

Figure 1:
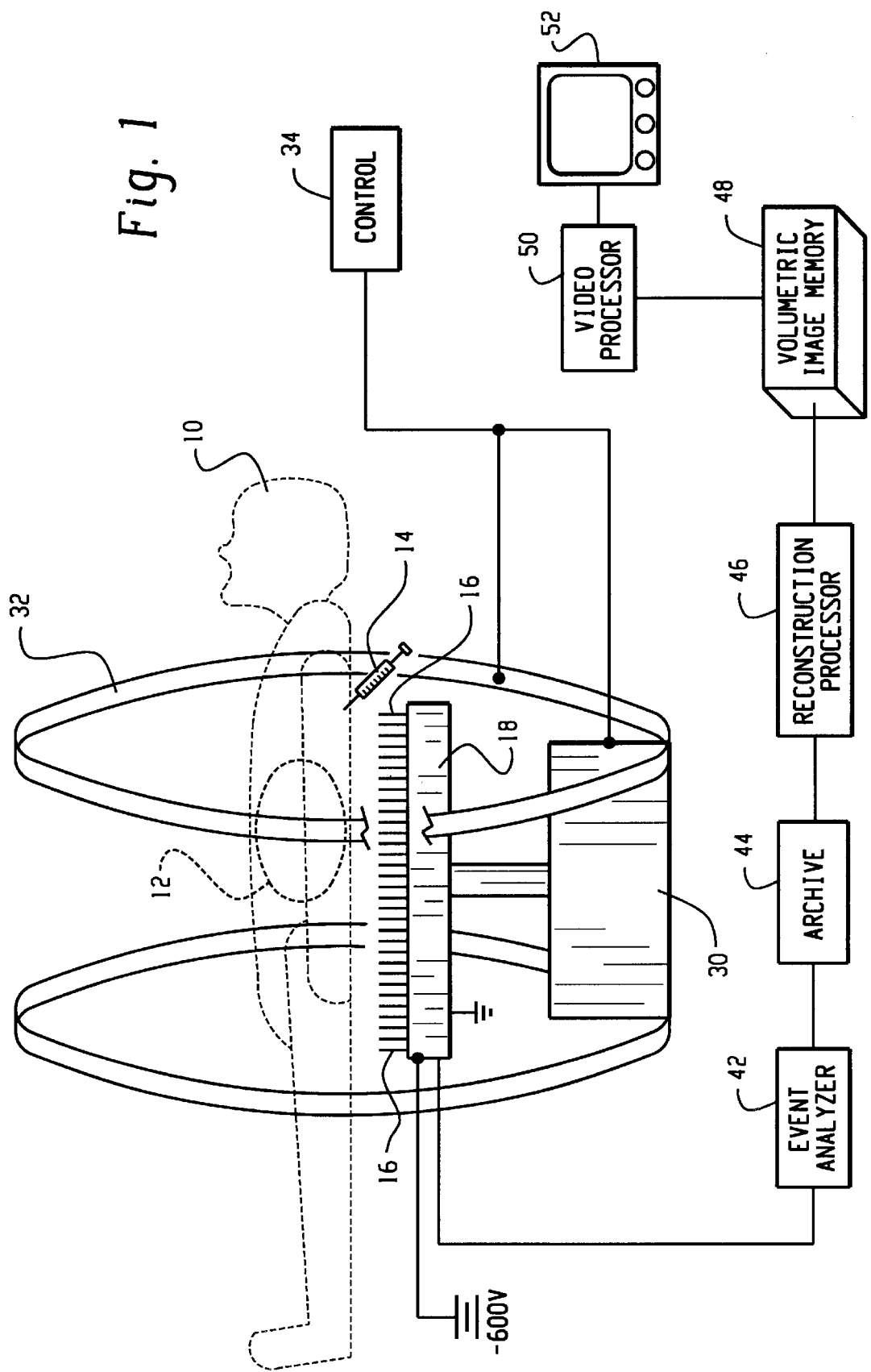
FIG. 1 is a diagrammatic illustration of a nuclear imaging device in accordance with the present invention.

With reference to FIG. 1, a subject 10 defines an imaging region 12. In the preferred embodiment, a radioactive pharmaceutical 14 is injected into the subject, near a region to be imaged. For example, if a physician wants to view a blockage in the aorta, the isotope is injected into the bloodstream upstream from the blockage. Image data is collected as the radiopharmaceutical moves with the blood to image the circulatory system. As another example, the radiopharmaceutical is injected into the circulatory system and selectively absorbed by tissue of interest. After an absorption period, image data is collected to image the tissue of interest and measure absorption rates.

As quantum physics predicts, atomic nuclei of the radioactive isotope decay over time. Energy is released at the time of decay in the form of a radiation photon, more specifically, a γ-ray of characteristic energy.

Many of the γ-rays produced during an imaging propagate in useless directions. However, large numbers of the γ-rays pass through collimators 16, thin tungsten vanes in the preferred embodiment, and strike a detector array 18. At times, such large numbers arrive in such a short time that detected events overlap. In the preferred embodiment and with reference to FIG. 2, the detector array 18 includes a 4×24 array of cadmium zinc telluride (CZT) crystal arrays 20, each having 4×8 individual detectors 22. When the γ-ray strikes the CZT crystal, electrons are released in a small avalanche. The freed electrons are drawn to an electrode or one side of CZT crystal forming a current pulse or spike.

In the preferred embodiments, the detector array 18 and collimators 16 are mounted on a mechanized drive 30 that moves the detector array with a detector head. Preferably, the array moves with lateral rotational components of motion, although various trajectories are contemplated. In some applications, the detector array is stationarily mounted within the head. The detector head is mounted to a movable gantry that is indexed or rotated slowly around the region of interest.

In the preferred embodiment, the detector head is mounted on a rotatable gantry 32 which extends fully around the subject 10. A motor control 34 selects a range of motion of the detector array 18, if any, within the rotatable gantry and rotation of the gantry 32 stepwise or continuously around the image region.

In SPECT imaging, the collimator 16 limits access to the detector array 18 to radiation following prescribed paths or trajectories to trajectories substantially parallel to the collimator vanes, preferably substantially perpendicular to the plane of the detector array 18. In this manner, each radiation event defines a trajectory that intersects the origin of the γ-ray, i.e. the origin of the event. If the movable gantry 32 remains stationary, the detectors define a projection image of the radioisotope distribution in the region of interest. An event analyzer 42 determines the location which each events strikes the detector array, i.e., which detector receives it and the amount of energy of the radiation event. The radiation events collected at each stationary position of the detector array are stored in an archive 44. When the rotatable gantry 32 is rotated to different angular positions around the subject, a plurality of projection images from different angular orientations are collected. A reconstruction processor 46 backprojects or otherwise reconstructs the data from the archive memory 44 into a volumetric image representation for storage in a volumetric image memory 48. A video processor 50 under operator control selectively withdraws portions of the volumetric image representation and converts them into appropriate form for display on a video or other human-readable monitor 52.

Figure 2:
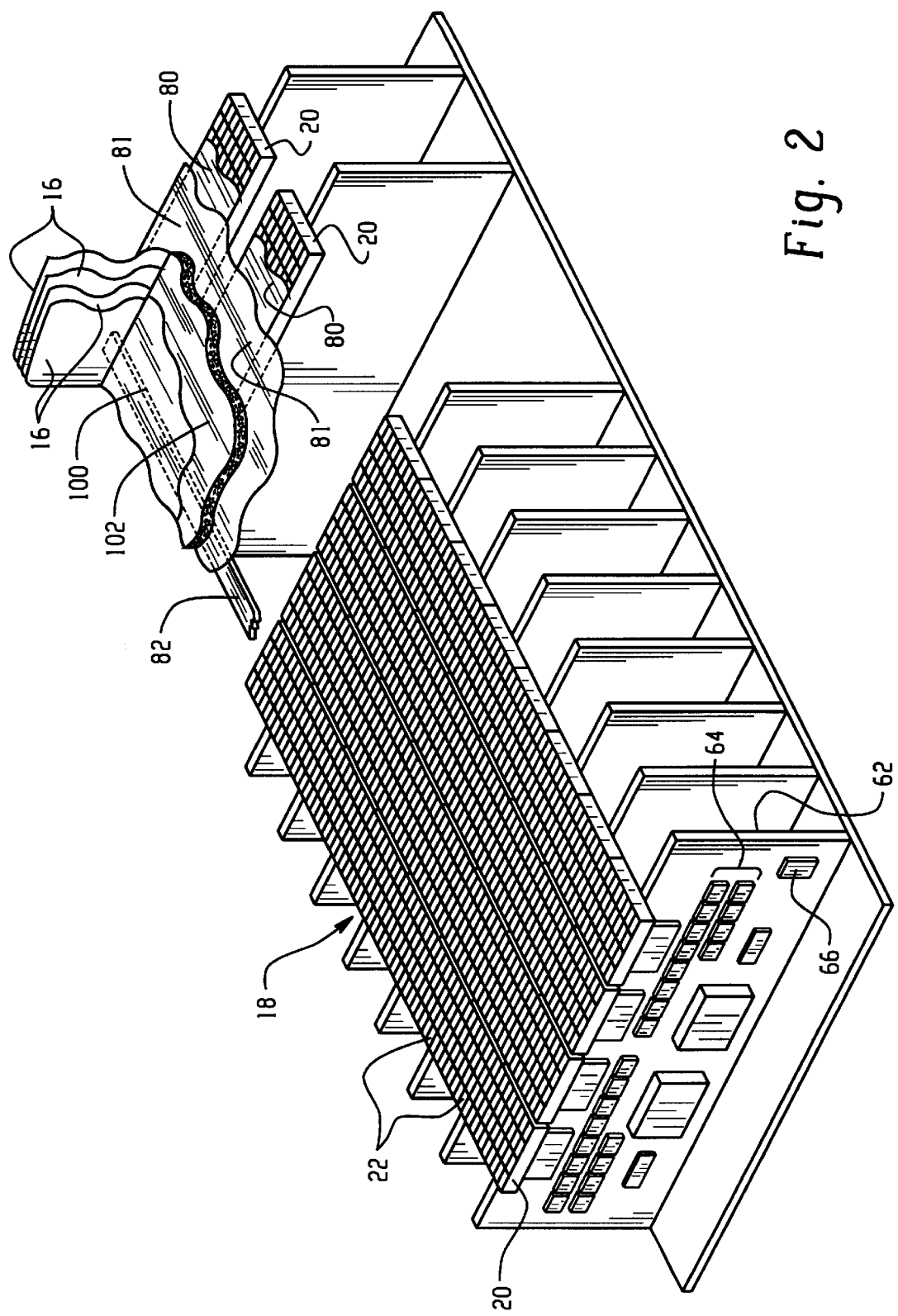
FIG. 2 is a perspective view of a detector array and circuit boards.
Figure 3:
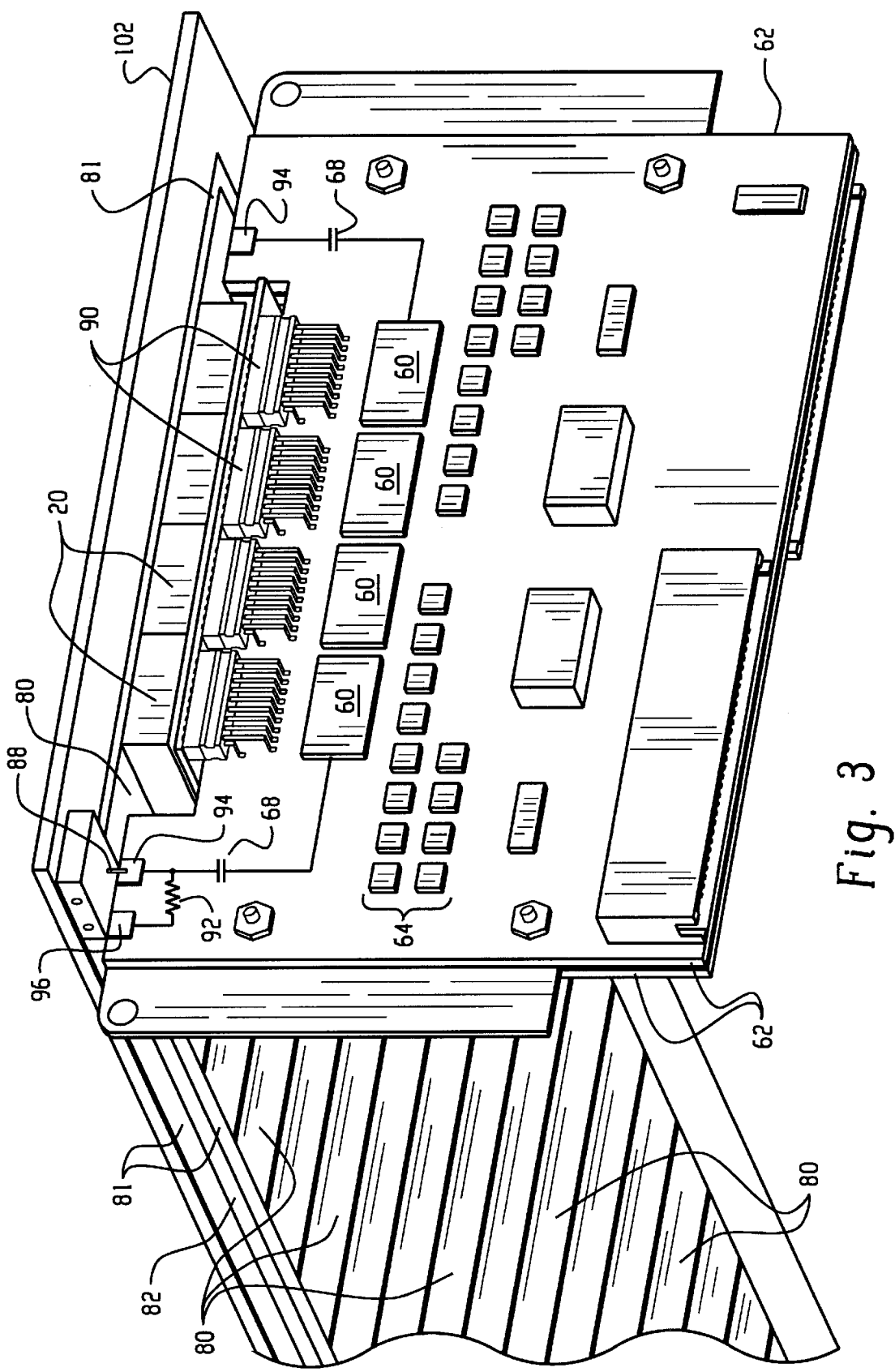
FIG. 3 is a perspective view of one of the circuit boards and detector array.

With reference to FIG. 3 and continuing reference to FIGS. 1 and 2, received γ-rays are detected and their energy measured by electronics attached to the detector array 18. In the preferred CZT embodiment, a potential difference of −600 V applied across the detector arrays by plurality of biasing strips 80, a high voltage busbar 82, a bias supply 84, and resistors 92. A secondary power supply 61 provides power to amplifier P-ASICs 60 located on circuit boards 62.

Each time a γ-ray strikes one of the detectors, an avalanche effect releases electrons producing an output electrical pulse. Associated electronic components 64 which are powered by a voltage regulator 66 spread the pulse, measure the area under the pulse, convert the area to a digital output, otherwise processes the received radiation data, and multiplex the digital data into a series of outputs to portions of the event analyzer 42 mounted remotely.

Figure 4:
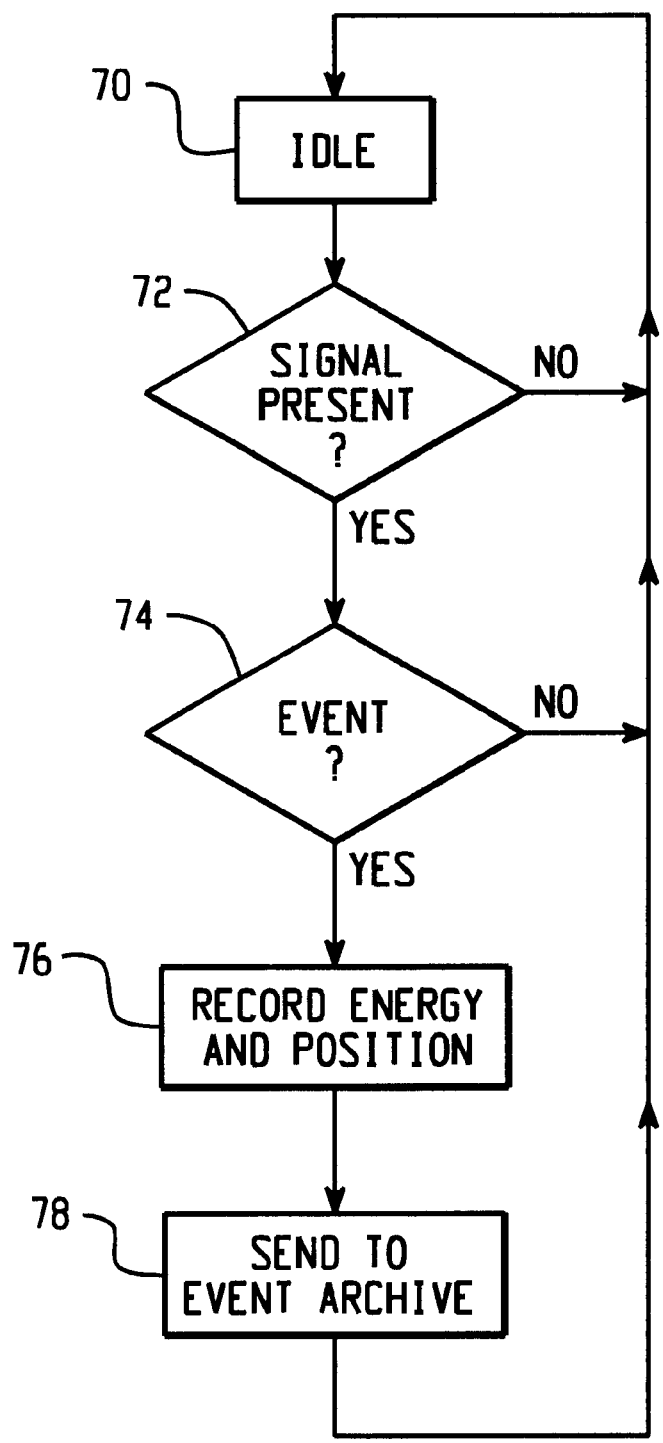
FIG. 4 is a flowchart of an event cycle on accordance with the present invention.

With reference to FIG. 4, in the preferred embodiment, the circuitry 64 or the remote portion of event analyzer 42 is normally idle 70, awaiting an electrical signal. When the event analyzer 42 receives an electrical signal, it compares it to a threshold 72. If the signal is less than the threshold, it is ignored as noise, and the analyzer 42 goes back to idle. If the signal is above the threshold, the analyzer classifies it as an event 74, and records 76 the energy of the signal, and the position of the detector 22 that sent the signal. The analyzer 42 then communicates 78 this information to the event archive 44 where it is held for reconstruction processing. After this communication, the analyzer 42 returns to idle awaiting the next event. In the preferred embodiment, once the analyzer 42 comes out of idle, in the next clock cycle, (preferably within 20 ns) other events are locked out until the analyzer 42 returns to idle. In the case of a true event, the process is completed, and the analyzer is back in idle in less than 2 µs. In the case of a false event, the analyzer 42 includes a timeout feature that only allows a set amount of time to determine the truth of an event. In the case of noise, the analyzer waits to see if the threshold is reached, but will return to idle within 2 µs of detecting the noise. The circuit 62 includes plural parallel channels, in the preferred embodiment a channel for each half of an array 20. In the instance of two or more simultaneous (within 20 ns of each other) events incident upon the same half of a detector array, both events are preferably discarded as difficult to isolate.

Figure 5:
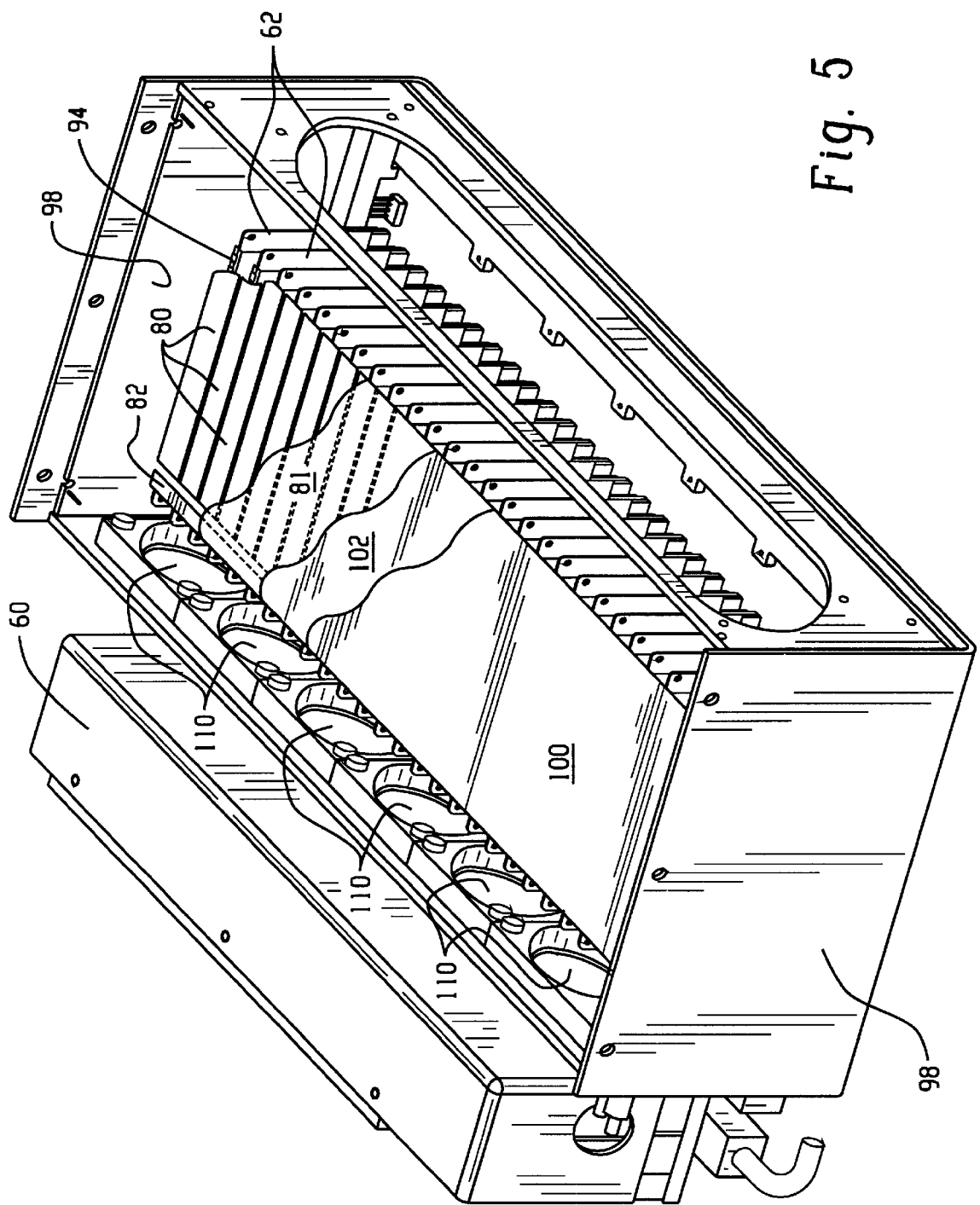
FIG. 5 is a perspective view of the detector array, circuit boards, and a bias grid.
Figure 6:
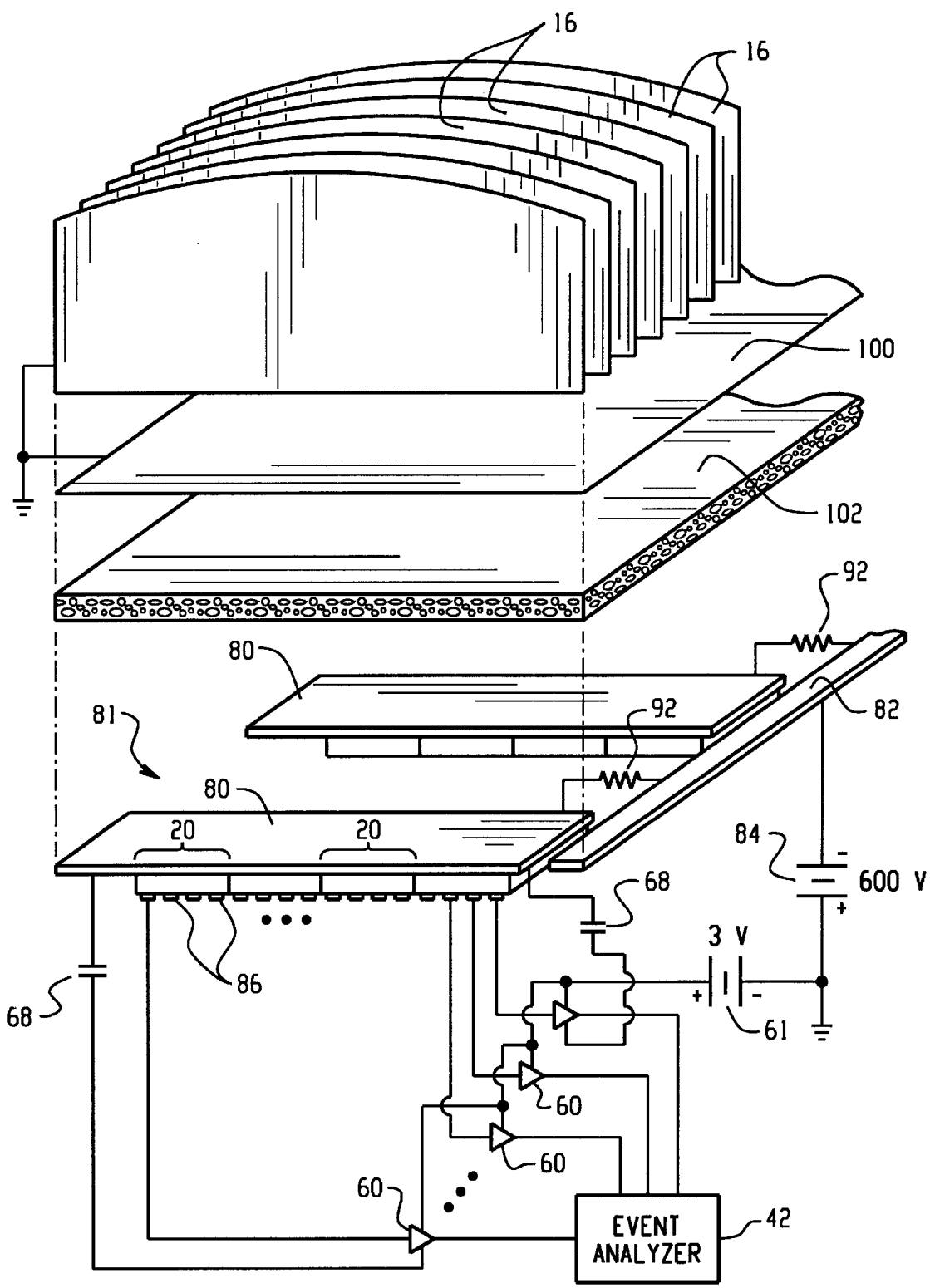
FIG. 6 is an expanded view illustrating detector arrays, electrical connections, and collimator mounting arrangement.

With continuing reference to FIGS. 2 and 3, and further reference to FIG. 5, each row of four detector arrays 20 has a common, upper electrical connector or conductive strip 80. In the preferred embodiment, the conductive strips 80 are thin layers of copper supported on a sheet 81 of mylar or other flexible insulator. The copper strips 80 cover an upper surface of each detector array uniformly, such that an even negative bias voltage is applied over the entire surface. The bias greatly aids the propagation of electrons through the detector array. The conducting strips 80 are connected by resistors 92 to a high voltage power supply busbar 82 which is also built on the mylar sheet 81. The high voltage busbar, in turn, is connected with the power supply 84 which biases the busbar 82 and the conductive strips 80 to −600 VDC, in the preferred embodiment. The other side of the power supply is also connected with the ground planes of the circuit boards 62. The busbar 82 is connected at one end with a contact pin 88 to facilitate electrical connection with the power supply 84. Making electrical contact by pressure against the pin 88 obviates the need for a physical wire and simplifies assembly and disassembly for repairs. An opposite face of each detector of each array 20 is an electrical contact with a conductive pad 86 which is held at a virtual ground. The conductive pads 86 are connected with electrical connectors or pins which are received in sockets 90 on the circuit board 62. When electrons are released in one of the crystals, the bias causes the released electrons to be attracted to the electrical pads 86. The electrical pads 86 are connected with amplifiers and other processing circuitry 64. In the preferred embodiment, each circuit board 62 is equipped with four P-ASICs 60 or other low level amplifiers that perform the amplification needed to analyze the electrical signals generated by the detector array 18.

The conductors 80 are, preferably, connected to the busbar 82 by a plurality of resistances 92, such that each of the conductive strips 80 is isolated from the other conductive strips. The capacitors 68 are connected between the conductive strips 80 of each Faraday cage and a ground connection of the amplifiers to form a noise filter. In the preferred embodiment, the capacitors 68 are sized relative to the other circuit components to provide a lowpass filter.

In the preferred embodiment, the mylar sheet 81 is positioned with the conductive strips 80 abutting four aligned CZT arrays and against contacts 94 on the circuit boards. The busbar strip 82 abuts the power receiving pin 88 and contacts 96 on the circuit boards. The resistors 92 are connected across contacts 94 and 96 and the capacitors 68 are connected to the contacts 94. Locating the capacitors 68 and the resistors 92 on circuit boards 62 allows the high voltage distribution busbar 82 and bias strips 80 to be implemented with a single removable sheet 80, 81, 82.

The conductive strips 80, the ground planes (a conductive layer within each circuit board) define a Faraday cage. Because the rows of detector arrays abut each other with no intervening source of stray noise, the central Faraday cages can be opened on the sides. Grounded metal end plates 98 of the housing close the Faraday cages at the ends of the array.

The tungsten main collimators 16 are connected with system ground. More specifically, the collimators 16 are mechanically pressed against an aluminum foil, screen, or other conductive sheet 100 which is connected with system ground. The ground sheet 100 rests on a layer of foam insulation 102 which with the mylar layer isolates the ground layer 100 from the −600 VDC biasing strips 80. The conductive sheet 100 also performs Faraday shielding functions.

The resilient foam 102 not only insulates the ground layer 100 from the conductive strips 80, but also provides a sufficient pressure to assure good electrical contact between the conductive strips 80 and contacts 94 and between bias strip 82 and contacts 88, 96.

The P-ASICs 60, in conjunction with the voltage regulators 66 and other circuit elements 64, when in operation, jointly produce a significant amount of heat. Having all of the components located on a circuit board running parallel to the detector would produce enough heat to damage or destroy the components. In the preferred embodiment, connector patterns in the crystal substrate are alternated to allow circuit boards 62 to be placed back to back perpendicular to the detector array 18, providing a much larger volume with which to dissipate heat. In the preferred embodiment, with reference to FIG. 5 a set of fans 110 on either or both sides of the assembly move outside air across the circuit boards 62 cooling the components located thereon.

With such a high bias voltage on the detector array 18, the CZT crystals become sensitive to many types of radiation, including visible light which enters easily via fan openings. In order to solve this problem, an opaque foam is used to construct a thermal and light shield for the detector array 18. An opaque foam is also expanded in open areas around the detector array, providing protection from light without relying on relatively space consumptive light baffles around the fans or other openings. In addition to blocking out light, this keeps board heat away from the CZT crystals, and also aids in the cooling, since space between circuit boards 62 can be used to move air through the system and cool the circuit boards 62.

In an alternate embodiment, the radioactive source is mounted and fixed on the opposite side of the subject across from the detector array. In this manner, the γ-rays which originate outside the subject either from a point or line source of radioactive material or a low power x-ray tube pass through the subject.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear imaging apparatus comprising;
   a detector system including an array of detector crystals which detect γ-ray radiation and generate electrical signals in response thereto;
   a Faraday cage shielding the detector crystals and related system elements;
   electronics that process the electrical signals; and,
   a reconstruction processor that processes the electrical signals into an image representation.

2. The nuclear imaging apparatus as set forth in claim 1, wherein the detector system includes a multi-channel cadmium-zinc-telluride array.

3. The nuclear imaging apparatus as set forth in claim 1, further including:
   tungsten plates disposed parallel with respect to one another for collimating the γ-rays in one dimension.

4. The nuclear imaging apparatus as set forth in claim 1, wherein the detector system comprises:
   a segmented array of solid state detectors;
   light shielding for blocking visible electromagnetic radiation from reaching the array of detectors; and,
   a bias grid for applying a voltage bias to the array of detectors.

5. The nuclear imaging apparatus as set forth in claim 4, wherein the detector system further includes:
   an array of high-z metal vanes disposed parallel to one another that collimate incoming radiation; and,
   an insulating cushion disposed between the biasing grid and the metal vanes.

6. The nuclear imaging apparatus as set forth in claim 4, wherein the bias grid comprises:
   a plurality of conducting strips disposed parallel with respect to one another; and,
   a power supply strip for supplying voltage to the conducting strips.

7. The nuclear imaging apparatus as set forth in claim 6 wherein the conducting strips and the power strip are affixed to a flexible insulating sheet.

8. The nuclear imaging system as set forth in claim 1, wherein the detector system includes a plurality of detector arrays, the plurality of detector arrays being shielded by a plurality of Faraday cages.

9. A nuclear imaging apparatus comprising:
   a detector system including a segmented array of solid state detectors that detects γ-ray radiation and generates electrical signals in response thereto;
   electronics that process the electrical signals;
   a bias grid that includes a plurality of conducting strips and a power supply strip for supplying voltage to the conducting strips, which bias grid applies a voltage bias to the array of detectors;

at least one capacitance connected between the conductive strip and ground to form a Faraday cage and reduce first order electrical noise generated by the bias grid; and, a reconstruction processor that processes the electrical signals into an image representation.

10. The nuclear imaging apparatus as set forth in claim 9, wherein the electronics includes a plurality of event analyzers, that determine the event information, the event information including:

a logical truth of a received event;

a location of its individual detector at a time of the received event; and, an energy of the received event.

11. A nuclear camera, comprising:

a plurality of arrays of solid state radiation detectors, each detector responding to receipt of γ-radiation by releasing electrons;

an electrically conductive biasing strip which covers all detectors of at least one of the arrays;

a plurality of conductive pads, electrically connected with detector surfaces opposite to the conductive biasing strip;

a voltage source connected between the electrically conductive biasing strip and the electrically conductive pads for applying a bias voltage, which attracts free electrons to the conductive pads;

signal processing circuitry connected with the electrically conductive pads for converting free electrons biased to the electrical pads into electronic data; and, a reconstruction processor connected with the processing circuitry for reconstructing the electronic data into image representations.

12. The nuclear camera as set forth in claim 11, further including a low frequency filter connected between each electrically conductive strip and ground.

13. The nuclear camera as set forth in claim 12, wherein the plurality of detector arrays are divided into groups, and further including a plurality of the conductive strips, one conductive strip connected with and covering a radiation receiving surface of each of the detectors of one of the groups.

14. The nuclear camera as set forth in claim 13, wherein each of the conductive strips are connected with a common power supply and further including:

resistive couplings for isolating the electrically conductive strips to define a plurality of Faraday cages.

15. The nuclear camera as set forth in claim 13 wherein the conductive strips are formed on a flexible insulating sheet.

16. A radiation detector assembly for use in conjunction with a nuclear imaging diagnostic device, the detector assembly comprising:

an array of detectors sensitive to radiation;

a bias circuit for applying high voltage potentials between a radiation receiving face and an opposite face of the detector array;

an electrically insulating layer disposed on a radiation receiving side of the bias circuit;

a ground layer mounted on a radiation receiving side of the insulating layer; and, high-z metal vanes for collimating incoming radiation mounted in engagement with the ground layer.

17. The detector assembly as set forth in claim 16, wherein the array of detectors is a solid state detector array comprising a plurality of cadmium zinc telluride crystal elements.

18. The detector assembly as set forth in claim 16, wherein the bias circuit includes:

conducting layers on the radiation receiving face of the array biased to a negative potential;

a capacitor that filters electrical signals generated by the array of detectors connected between the conducting layer and ground.

19. A nuclear imaging apparatus comprising:

a plurality of detector arrays shielded by a plurality of Faraday cages, the detector arrays generating electrical signals in response to detecting γ-ray, radiation;

a low frequency filter connected with each of the Faraday cages;

electronics that process the electrical signals; and, a reconstruction processor that processes the electrical signals into an image representation.

20. A nuclear imaging apparatus comprising:

a segmented array of solid state detectors;

a bias grid for applying a voltage bias to the array of detectors;

an array of metal vanes that collimate incoming radiation;

an insulating cushion disposed between the biasing grid and the metal vanes;

a conductive ground sheet on the surface of the insulating cushion adjacent the metal vanes;

opaque foam blocking light and heat from reaching the array of detectors;

electronics that process the electrical signals; and, a reconstruction processor that processes the electrical signals into an image representation.

21. A detector assembly for use in conjunction with a nuclear imaging diagnostic device, the detector assembly comprising:

an array of detectors sensitive to radiation, the array of detectors including a plurality of detector groups;

a discrete conducting layer on the radiation receiving face of each group of detectors, the conducting layer biased to a negative potential;

capacitors connected between each of the conductive layers and ground that filter electrical signals generated by the array of detectors connected between the conducting layer and ground;

an electrically insulating layer disposed on a radiation receiving side of the conducting layers;

a ground layer mounted on a radiation receiving side of the insulating layer;

a plurality of resistive elements for electrically isolating each of the conducting layers to define a plurality of Faraday cages.

22. A method of nuclear imaging comprising:

applying a bias voltage between a radiation receiving face and an opposite face of an array of solid state radiation detectors;

filtering the bias voltage with a low frequency filter to remove noise;

responding to incident radiation which penetrates the solid state detectors with a current pulse; and, processing and reconstructing the current pulses into an image representation.

* * * * *